`US010893792B2`

(12) United States Patent
Iwaki (10) Patent No.: US 10,893,792 B2
(45) Date of Patent: *Jan. 19, 2021

(54) ENDOSCOPE IMAGE PROCESSING APPARATUS AND ENDOSCOPE IMAGE PROCESSING METHOD

(71) Applicant: OLYMPUS CORPORATION, Hachioji (JP)

(72) Inventor: Hidekazu Iwaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/389,581

(22) Filed: Apr. 19, 2019

(65) Prior Publication Data

US 2019/0239718 A1 Aug. 8, 2019

Related U.S. Application Data

(63) Continuation of application No. PCT/JP2016/081608, filed on Oct. 25, 2016.

(51) Int. Cl.
*A61B 1/04* (2006.01)
*A61B 1/00* (2006.01)
(Continued)

(52) U.S. Cl.
CPC ............ *A61B 1/00009* (2013.01); *A61B 1/04* (2013.01); *A61B 1/05* (2013.01); *A61B 1/0676* (2013.01);
(Continued)

(58) Field of Classification Search
CPC ......... A61B 1/00009; A61B 1/04; A61B 1/05; A61B 1/0676; G02B 23/2461
(Continued)

(56) References Cited

U.S. PATENT DOCUMENTS

2011/0254937 A1 10/2011 Yoshino
2012/0274754 A1 11/2012 Tsuruoka
2018/0249900 A1 9/2018 Imaizumi et al.

FOREIGN PATENT DOCUMENTS

EP 2517614 A1 10/2012
JP 2009142552 A 7/2009
(Continued)

OTHER PUBLICATIONS

JP2011036371 Machine Translation (Year: 2011).*
(Continued)

*Primary Examiner* — Nguyen T Truong
(74) *Attorney, Agent, or Firm* — Holtz, Holtz & Volek PC (57) ABSTRACT

An endoscope image processing apparatus includes a region-of-interest detection apparatus configured to sequentially receive observation images obtained by performing image pickup of an object and perform processing for detecting a region of interest for each of the observation images, and a processor. The processor calculates an appearance time period as an elapsed time period from a time when the region of interest appears within the observation image when the region-of-interest detection apparatus detects the region of interest, and starts emphasis processing for emphasizing a position of the region of interest existing within the observation image at a timing at which the appearance time period reaches a predetermined time period.

4 Claims, 6 Drawing Sheets

(51) Int. Cl.
    *A61B 1/06* (2006.01)
    *G02B 23/24* (2006.01)
    *A61B 1/05* (2006.01)
    *G16H 30/40* (2018.01)
(52) U.S. Cl.
    CPC ...... *G02B 23/2461* (2013.01); *G02B 23/2484* (2013.01); *G16H 30/40* (2018.01)
(58) Field of Classification Search
    USPC .......................................................... 348/65
    See application file for complete search history.

(56) References Cited

FOREIGN PATENT DOCUMENTS

| | | |
|---|---|---|
| JP | 2011036371 A | 2/2011 |
| JP | 2011160848 A | 8/2011 |
| JP | 2011224038 A | 11/2011 |
| JP | 2011255006 A | 12/2011 |
| WO | 2011096279 A1 | 8/2011 |
| WO | 2017081976 A1 | 5/2017 |

OTHER PUBLICATIONS

International Search Report (ISR) dated Jan. 24, 2017 issued in International Application No. PCT/JP2016/081608.
Written Opinion dated Jan. 24, 2017 issued in International Application No. PCT/JP2016/081608.

* cited by examiner

| EVALUATION VALUE E | AVERAGE DETECTION TIME AT |
|---|---|
| Ea | ATa |
| Eb | ATb |
| Ec | ATc |
| ⋮ | ⋮ |

TDA

ENDOSCOPE IMAGE PROCESSING APPARATUS AND ENDOSCOPE IMAGE PROCESSING METHOD

CROSS REFERENCE TO RELATED APPLICATION

This application is a continuation application of PCT/JP2016/081608 filed on Oct. 25, 2016, the entire contents of which are incorporated herein by this reference.

BACKGROUND OF THE INVENTION

1. Field of the Invention

The present invention relates to an endoscope image processing apparatus and an endoscope image processing method.

2. Description of the Related Art

Conventionally, in an endoscope apparatus, an operator has determined presence or absence of a lesion portion, for example, by viewing an observation image. To prevent the lesion portion from being overlooked when the operator views the observation image, an endoscope apparatus which displays an observation image by adding an alert image to a region of interest detected by image processing has been proposed, as described in Japanese Patent Application Laid-Open Publication No. 2011-255006, for example.

SUMMARY OF THE INVENTION

An endoscope image processing apparatus according to an aspect of the present invention includes a region-of-interest detection apparatus configured to sequentially receive observation images obtained by performing image pickup of an object and perform processing for detecting a region of interest for each of the observation images, and a processor, in which the processor is configured to calculate an appearance time period as an elapsed time period from the time when the region of interest appears within the observation image when the region-of-interest detection apparatus detects the region of interest, and start emphasis processing for emphasizing a position of the region of interest existing within the observation image at a timing at which the appearance time period reaches a predetermined time period.

An endoscope image processing method according to an aspect of the present invention includes performing processing for detecting a region of interest for each of observation images obtained by performing image pickup of an object, calculating an appearance time period as an elapsed time period from a time when the region of interest appears within the observation image when the region of interest is detected, and starting emphasis processing for emphasizing a position of the region of interest existing within the observation image at a timing at which the appearance time period reaches a predetermined time period.

DETAILED DESCRIPTION OF THE PREFERRED EMBODIMENT

An embodiment of the present invention will be described below with reference to the drawings.

Figure 1:
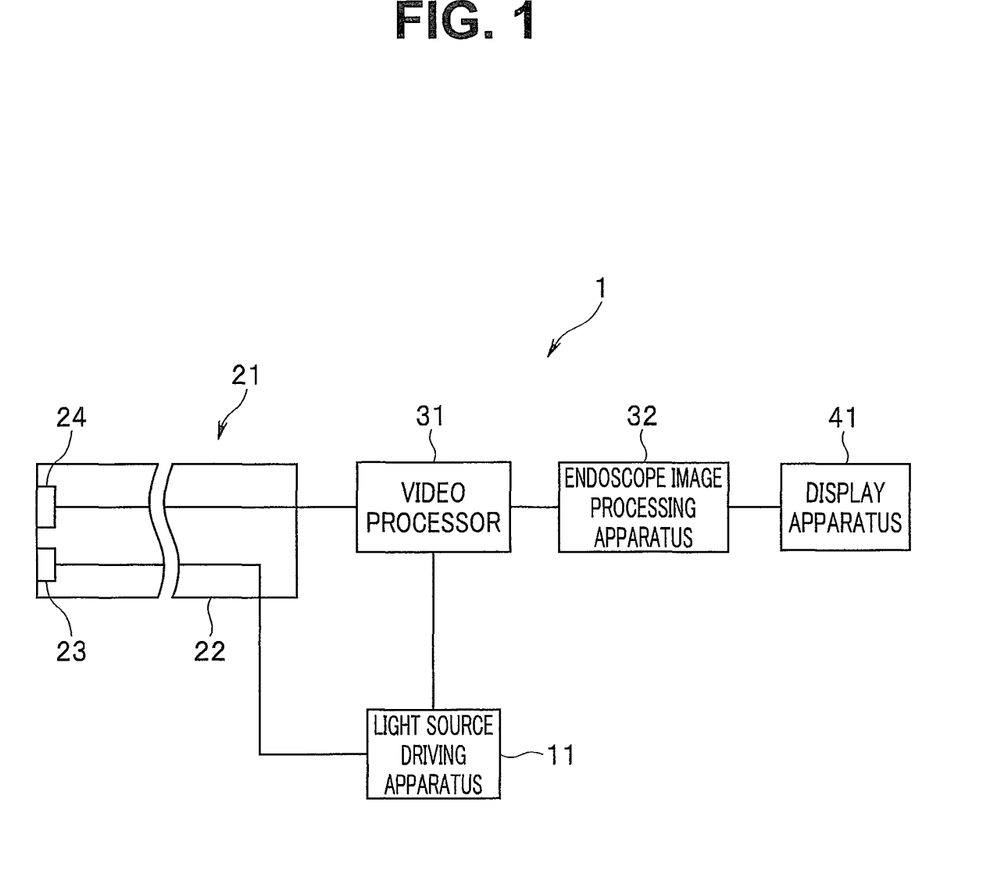
FIG. 1 is a diagram illustrating a configuration of a principal part of an endoscope system including an endoscope image processing apparatus according to an embodiment.

An endoscope system 1 is configured to include a light source driving apparatus 11, an endoscope 21, a video processor 31, an endoscope image processing apparatus 32, and a display apparatus 41, as illustrated in FIG. 1. FIG. 1 is a diagram illustrating a configuration of a principal part of the endoscope system including the endoscope image processing apparatus according to the embodiment.

The light source driving apparatus 11 is configured to include a drive circuit, for example. The light source driving apparatus 11 is connected to the endoscope 21 and the video processor 31. The light source driving apparatus 11 is configured to generate a light source driving signal for driving a light source section 23 in the endoscope 21 based on a light source control signal from the video processor 31 and output the generated light source driving signal to the endoscope 21.

The endoscope 21 is connected to the light source driving apparatus 11 and the video processor 31. The endoscope 21 is configured to include an elongated insertion section 22 insertable into a body cavity of a subject. The light source section 23 and an image pickup section 24 are provided in a distal end portion of the insertion section 22.

The light source section 23 is configured to include a light emitting element such as a white LED (light emitting diode). The light source section 23 is configured to emit light in response to the light source driving signal outputted from the light source driving apparatus 11 to generate illumination light and emit the generated illumination light to an object such as a living tissue.

The image pickup section 24 is configured to include an image sensor such as a color CCD (charge-coupled device) or a color CMOS (complementary metal oxide semiconductor). The image pickup section 24 is configured to perform an operation in response to an image pickup control signal outputted from the video processor 31. The image pickup section 24 is configured to receive reflected light from the object illuminated by the illumination light from the light source section 23, pick up an image of the received reflected light to generate an image pickup signal, and output the generated image pickup signal to the video processor 31.

The video processor 31 is connected to the light source driving apparatus 11 and the endoscope 21. The video processor 31 is configured to generate a light source control signal for controlling a light emitting state of the light source section 23 and output the generated light source control signal to the light source driving apparatus 11. The video processor 31 is configured to generate and output an image pickup control signal for controlling an image pickup operation of the image pickup section 24. The video processor 31 is configured to subject an image pickup signal outputted from the endoscope 21 to predetermined processing to generate observation images G1 of the object and sequentially output the generated observation images G1 to the endoscope image processing apparatus 32 for each frame.

Figure 2:
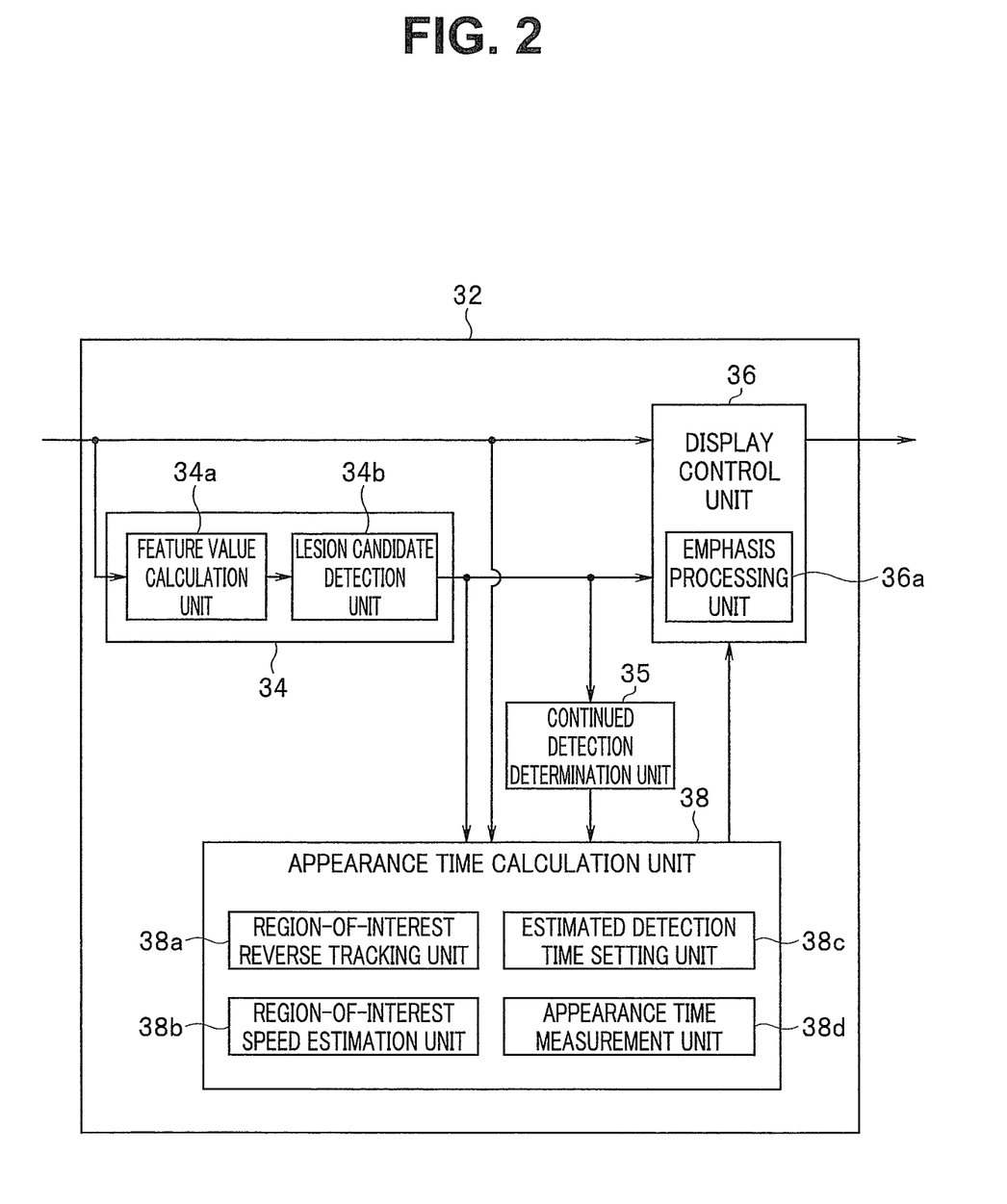
FIG. 2 is a block diagram for describing an example of a specific configuration of the endoscope image processing apparatus according to the embodiment.

The endoscope image processing apparatus 32 is configured to perform an operation for generating a display image based on the observation image G1 outputted from the video processor 31 and displaying the generated display image on the display apparatus 41. The endoscope image processing apparatus 32 is configured to include a region-of-interest detection unit 34, a continued detection determination unit 35, a display control unit 36, and an appearance time calculation unit 38. Note that according to the present embodiment, each of the units in the endoscope image processing apparatus 32 may be configured as an individual electronic circuit or may be configured as a circuit block in an integrated circuit such as an FPGA (field programmable gate array). According to the present embodiment, at least a part of the endoscope image processing apparatus 32 may be composed of a CPU (central processing unit), for example. FIG. 2 is a block diagram for illustrating an example of a specific configuration of the endoscope image processing apparatus according to the embodiment.

The region-of-interest detection unit 34 is configured to calculate a predetermined feature value relating to each of the observation images G1 sequentially outputted from the video processor 31 and further detect a lesion candidate region L as a region of interest included in an observation image G1 based on the calculated predetermined feature value. That is, the region-of-interest detection unit 34 is configured to sequentially receive the plurality of observation images G1 obtained by performing image pickup of the object using the endoscope 21 while performing processing for detecting the lesion candidate region L for each of the plurality of observation images G1. The region-of-interest detection unit 34 is configured to include a feature value calculation unit 34*a* and a lesion candidate detection unit 34*b*, as illustrated in FIG. 2.

The feature value calculation unit 34*a* is configured to calculate the predetermined feature value relating to each of the observation images G1 sequentially outputted from the video processor 31 and output the calculated predetermined feature value to the lesion candidate detection unit 34*b*.

More specifically, the feature value calculation unit 34*a* calculates a slope value as a value representing an amount of change in luminance or an amount of change in concentration between each of pixels within one of a plurality of small regions obtained by dividing the observation image G1 in a predetermined size and each of pixels within the small region adjacent to the one small region as a feature value for each of the plurality of small regions. Note that the feature value calculation unit 34*a* may calculate a value different from the above-described slope value as a feature value as long as the feature value calculation unit 34*a* calculates a value at which the observation image G1 can be quantitatively evaluated.

The lesion candidate detection unit 34*b* is configured to include a nonvolatile memory (not illustrated) such as a ROM (read-only memory) previously storing one or more pieces of polyp model information.

More specifically, each piece of the polyp model information stored in the memory in the lesion candidate detection unit 34*b* is configured to include a feature value obtained by quantifying a common point and/or respective similar points in many polyp images, for example.

The lesion candidate detection unit 34*b* is configured to detect a lesion candidate region L based on the predetermined feature values outputted from the feature value calculation unit 34*a* and the plural pieces of polyp model information read from the memory, acquire lesion candidate information IL as information representing the detected lesion candidate region L, and output the acquired lesion candidate information IL to each of the continued detection determination unit 35, the display control unit 36, and the appearance time calculation unit 38.

More specifically, the lesion candidate detection unit 34*b* detects, when the feature value in the one small region outputted from the feature value calculation unit 34*a* and at least one of the feature values included in the plural pieces of polyp model information read from the memory match each other, for example, the one small region as a lesion candidate region L. The lesion candidate detection unit 34*b* acquires lesion candidate information IL including position information and size information of the lesion candidate region L detected using the above-described method and outputs the acquired lesion candidate information IL to each of the continued detection determination unit 35, the display control unit 36, and the appearance time calculation unit 38.

Note that the position information of the lesion candidate region L is information representing a position of the lesion candidate region L within the observation image G1, and is acquired as a pixel position in the lesion candidate region L existing within the observation image G1, for example. The size information of the lesion candidate region L is information representing a size of the lesion candidate region L within the observation image G1, and is acquired as a number of pixels in the lesion candidate region L existing in the observation image G1, for example.

Note that the region-of-interest detection unit 34 need not be configured to include the feature value calculation unit 34*a* and the lesion candidate detection unit 34*b* as long as the region-of-interest detection unit 34 performs processing for detecting the lesion candidate region L from the observation image G1. More specifically, the region-of-interest detection unit 34 may be configured to perform processing for applying an image identifier, which has previously acquired a function of making a polyp image identifiable using a learning method such as deep learning, to the observation image G1 to detect the lesion candidate region L from the observation image G1.

The continued detection determination unit 35 is configured to include a volatile memory (not illustrated) such as a RAM (random access memory) capable of storing, among the lesion candidate information IL outputted from the lesion candidate detection unit 34*b*, the lesion candidate information IL in a frame preceding the current frame by one frame.

The continued detection determination unit 35 is configured to determine, based on first lesion candidate information outputted from the lesion candidate detection unit 34b and second lesion candidate information, stored in the memory, preceding the first lesion candidate information by one frame, for example, whether a first lesion candidate region represented by the first lesion candidate information and a second lesion candidate region represented by the second lesion candidate information are the same lesion candidate region L. The continued detection determination unit 35 is configured to acquire a determination result that the detection of the lesion candidate region L in the observation image G1 has been continued when the above-described first and second lesion candidate regions are the same lesion candidate region L and output the acquired determination result to the appearance time calculation unit 38. The continued detection determination unit 35 is configured to acquire a determination result that the detection of the lesion candidate region L in the observation image G1 has been discontinued when the above-described first and second lesion candidate regions are not the same lesion candidate region L and output the acquired determination result to the appearance time calculation unit 38.

The display control unit 36 is configured to perform processing for generating a display image using each of the observation images G1 sequentially outputted from the video processor 31 while performing processing for displaying the generated display image on a display screen 41A of the display apparatus 41. The display control unit 36 is configured to perform, based on the observation images G1 sequentially outputted from the video processor 31, the lesion candidate information IL outputted from the lesion candidate detection unit 34b, and an appearance time period TS (described below) outputted from the appearance time calculation unit 38, emphasis processing (described below) for emphasizing the lesion candidate region L existing within each of the observation images G1 in the emphasis processing unit 36a while displaying a display image, which has been subjected to the emphasis processing, on the display screen 41A of the display apparatus 41.

The emphasis processing unit 36a is configured to start emphasis processing as processing for generating a marker image G2 for emphasizing a position of the lesion candidate region L existing within the observation image G1 and adding the generated marker image G2 to the observation image G1 based on the lesion candidate information IL at a timing at which the appearance time period TS has reached a predetermined time period TH (e.g., 0.5 second).

Note that the marker image G2 added by the emphasis processing of the emphasis processing unit 36a may have any form as long as the position of the lesion candidate region L can be presented as visual information. In other words, the emphasis processing unit 36a may perform emphasis processing using only the position information included in the lesion candidate information IL or may perform emphasis processing using both the position information and the size information included in the lesion candidate information IL as long as the emphasis processing unit 36a generates the marker image G2 for emphasizing the position of the lesion candidate region L.

The appearance time calculation unit 38 is configured to perform processing for calculating, based on the observation images G1 sequentially outputted from the video processor 31, the lesion candidate information IL outputted from the lesion candidate detection unit 34b, and the determination result outputted from the continued detection determination unit 35, the appearance time period TS as an elapsed time period from appearance of the lesion candidate region L represented by the lesion candidate information IL within each of the observation images G1 when the lesion candidate region L is detected. The appearance time calculation unit 38 is configured to output the appearance time period TS obtained by the above-described processing to the display control unit 36. The appearance time calculation unit 38 is configured to include a region-of-interest reverse tracking unit 38a, a region-of-interest speed estimation unit 38b, an estimated detection time setting unit 38c, and an appearance time measurement unit 38d, as illustrated in FIG. 2.

The region-of-interest reverse tracking unit 38a is configured to perform processing for acquiring, based on the observation images G1 sequentially outputted from the video processor 31, an optical flow of each of the observation images G1 as a vector field constituted by motion vectors of all pixels included in the observation image G1 for each frame. The region-of-interest reverse tracking unit 38a is configured to include a volatile memory (not illustrated) such as a RAM capable of storing the observation images G1 sequentially outputted from the video processor 31 and the respective optical flows of the observation images G1 in chronological order and over a plurality of frames. The region-of-interest reverse tracking unit 38a is configured to perform processing (described below) for calculating, based on the optical flow of the current observation image G1 acquired as described above, respective optical flows of observation images G1 in the past corresponding to one or a plurality of frames stored in the memory, and the lesion candidate information IL outputted from the lesion candidate detection unit 34b, an image input time period TP as a time period from input of observation image G1, in which the lesion candidate region L first appears, until input of the current observation image G1.

The region-of-interest speed estimation unit 38b is configured to perform processing for acquiring, based on the observation images G1 sequentially outputted from the video processor 31, the optical flow of each of the observation images G1 as a vector field constituted by motion vectors of all pixels included in the observation image G1 for each frame. The region-of-interest speed estimation unit 38b is configured to include a volatile memory such as a RAM capable of storing the observation images G1 sequentially outputted from the video processor 31 in chronological order and over a plurality of frames. The region-of-interest speed estimation unit 38b is configured to perform processing (described below) for calculating, based on the lesion candidate information IL outputted from the lesion candidate detection unit 34b and the optical flow of the current observation image G1 acquired as described above, an estimated movement speed VQ of the lesion candidate region L.

The estimated detection time setting unit 38c is configured to perform processing (described below) for setting, based on the observation images G1 sequentially outputted from the video processor 31 and the lesion candidate information IL outputted from the lesion candidate detection unit 34b, an estimated detection time period TM as a time period estimated to be required to detect the lesion candidate region L in the lesion candidate detection unit 34b.

The appearance time measurement unit 38d is configured to measure a continued detection time period TK as an elapsed time period from when the region-of-interest detection unit 34 started to detect the lesion candidate region L based on the determination result outputted from the continued detection determination unit 35 when the lesion candidate information IL is inputted from the lesion candidate detection unit 34b. The appearance time measurement unit 38d is configured to perform processing (described below) for calculating, based on the image input time period TP calculated by the region-of-interest reverse tracking unit 38a, the estimated movement speed VQ calculated by the region-of-interest speed estimation unit 38b, the estimated detection time period TM set by the estimated detection time setting unit 38c, and the continued detection time period TK measured as described above, an appearance time period TS.

The display apparatus 41 includes a monitor, for example, and is configured to enable the display image outputted from the endoscope image processing apparatus 32 to be displayed on the screen.

Figure 3:
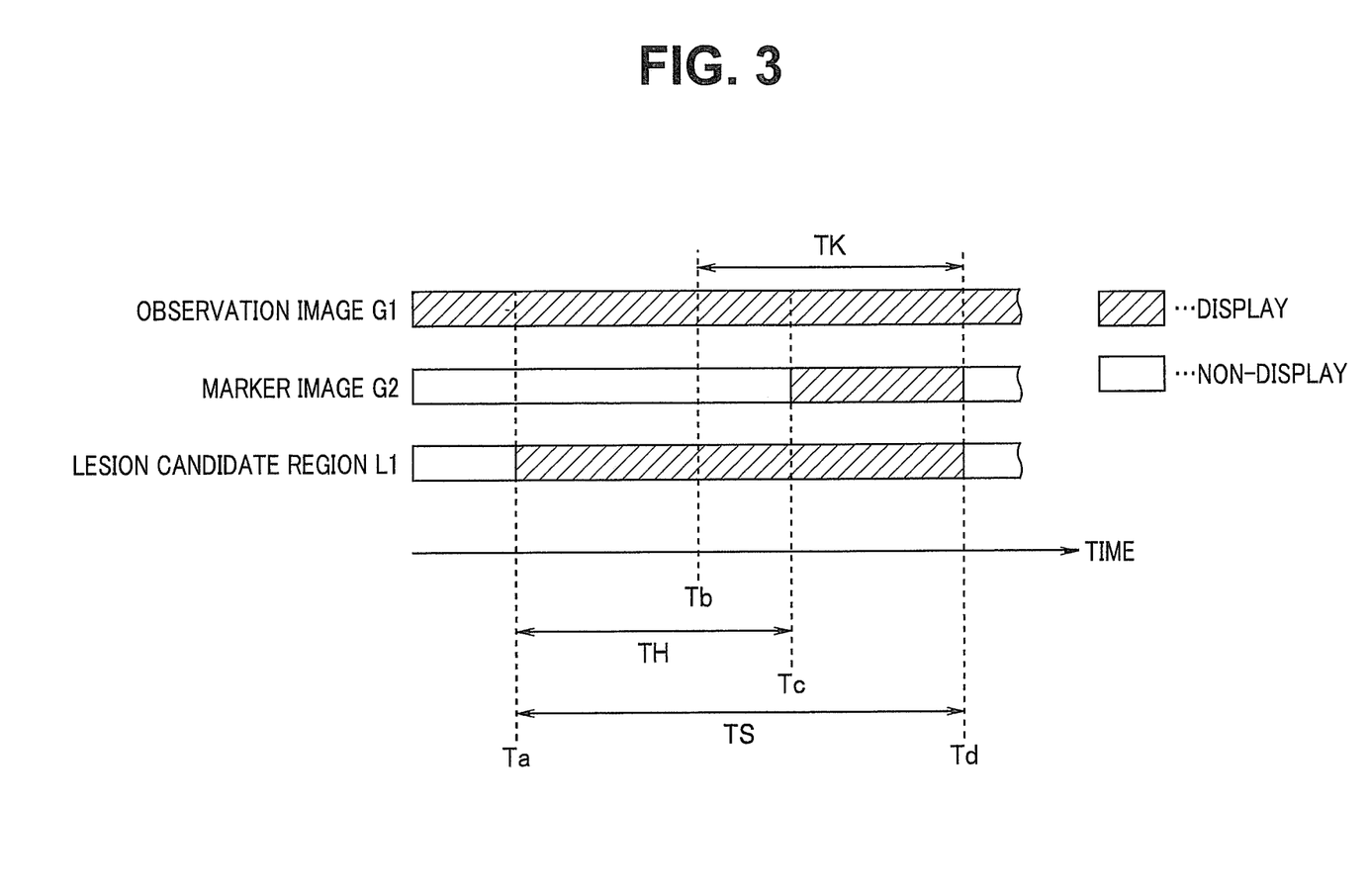
FIG. 3 is a diagram illustrating an example of processing performed in the endoscope image processing apparatus according to the embodiment.

Then, a function of the present embodiment will be described while referring to FIG. 3, for example, as needed. Note that description is made below by taking a case where one lesion candidate region L1 appears within an observation image G1 as an example for simplicity. FIG. 3 is a diagram for describing one example of processing performed in the endoscope image processing apparatus according to the embodiment.

The endoscope 21 emits illumination light to an object, receives reflected light from the object, picks up an image of the received reflected light to generate an image pickup signal, and outputs the generated image pickup signal to the video processor 31 when respective powers to the light source driving apparatus 11 and the video processor 31 are turned on, for example.

The video processor 31 subjects the image pickup signal outputted from the endoscope 21 to predetermined processing to generate observation images G1 of the object, and sequentially outputs the generated observation images G1 to the image processing apparatus 32 for each frame.

Figure 4:
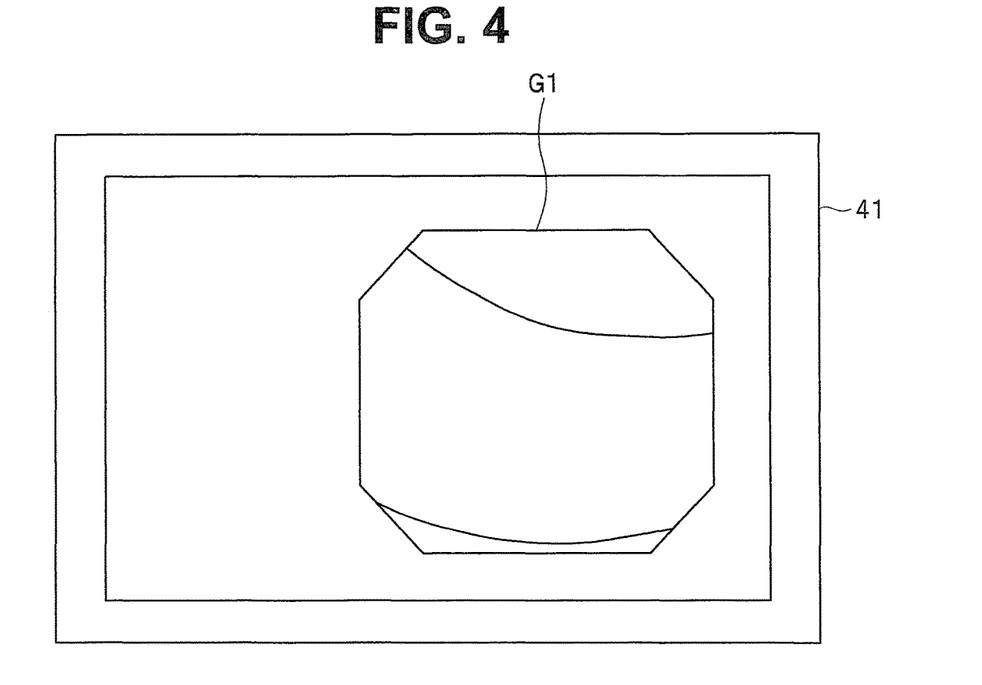
FIG. 4 is a diagram illustrating an example of a display image displayed on a display apparatus through the processing performed in the endoscope image processing apparatus according to the embodiment.
Figure 5:
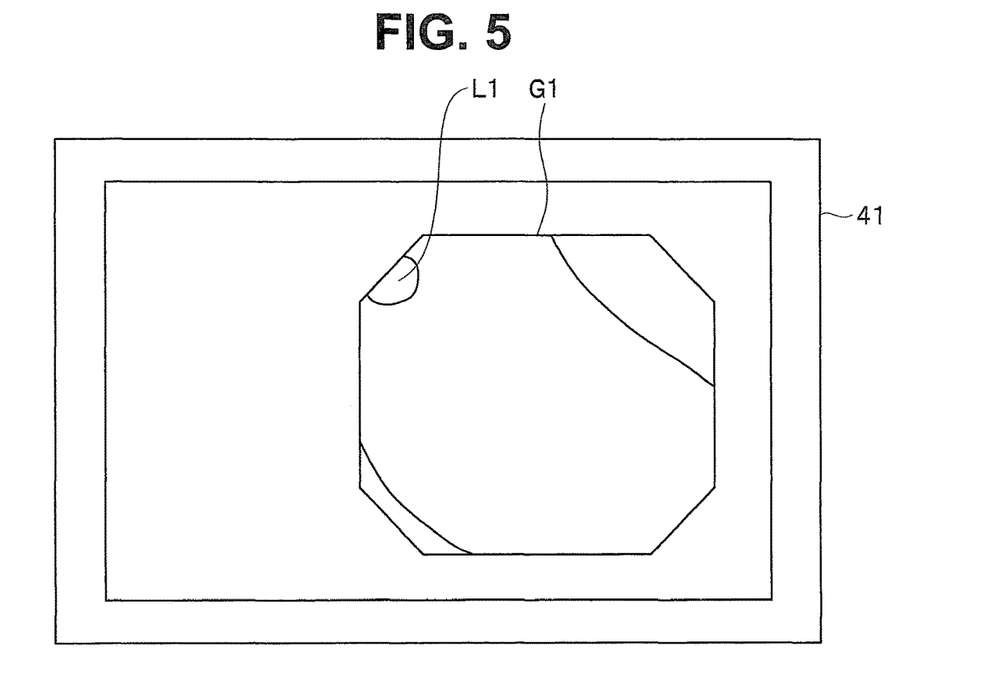
FIG. 5 is a diagram illustrating an example of a display image displayed on the display apparatus through the processing performed in the endoscope image processing apparatus according to the embodiment.

The display control unit 36 performs processing for displaying a display image including an observation image G1 as illustrated in FIG. 4, for example, on the display apparatus 41 in a period during which a lesion candidate region L1 does not appear within the observation image G1, i.e., a period before the time Ta illustrated in FIG. 3. The display control unit 36 performs processing for displaying a display image including an observation image G1 as illustrated in FIG. 5, for example, on the display apparatus 41 at a timing at which at least a part of a lesion candidate region L1 has appeared within the observation image G1, i.e., at a timing of the time Ta illustrated in FIG. 3. FIGS. 4 and 5 are diagrams each illustrating an example of a display image displayed on the display apparatus through the processing performed in the endoscope image processing apparatus according to the embodiment.

The lesion candidate detection unit 34b detects the lesion candidate region L1, which has appeared within the observation image G1, acquires lesion candidate information IL1 as information representing the detected lesion candidate region L1, and outputs the acquired lesion candidate information IL1 to each of the continued detection determination unit 35, the display control unit 36, and the appearance time calculation unit 38 at a timing of the time Tb later than the time Ta illustrated in FIG. 3.

Figure 6:
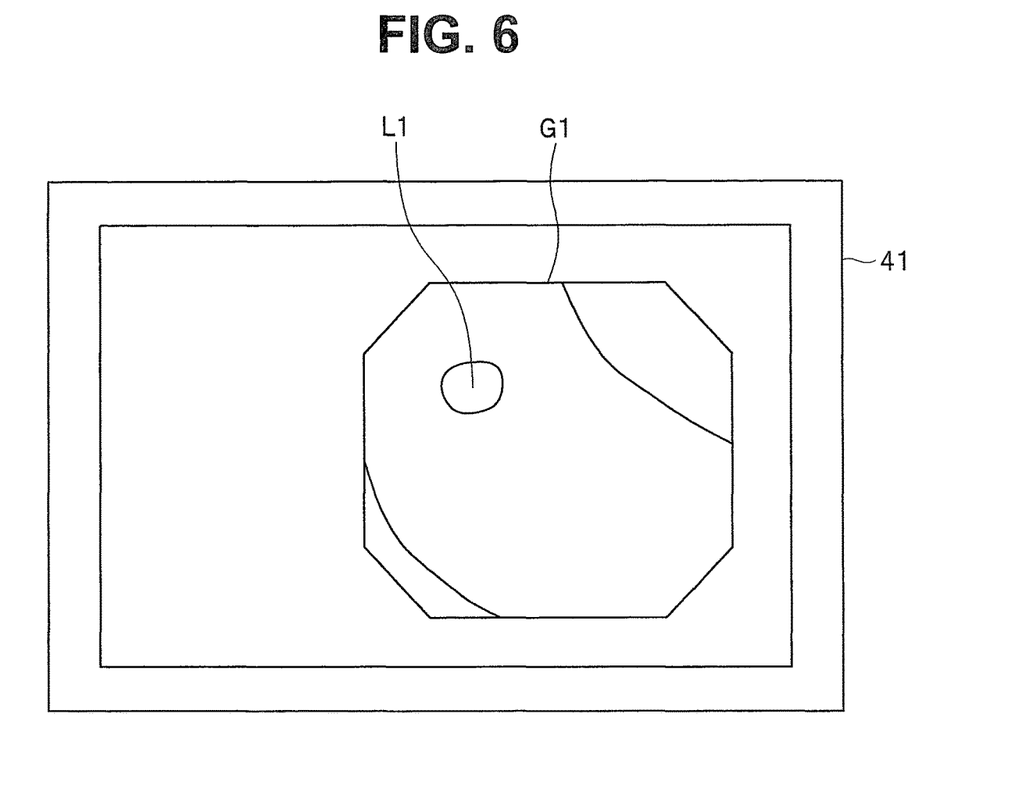
FIG. 6 is a diagram illustrating an example of a display image displayed on the display apparatus through the processing performed in the endoscope image processing apparatus according to the embodiment.

The display control unit 36 performs processing for displaying a display image including an observation image G1 as illustrated in FIG. 6, for example, on the display apparatus 41 at a timing of the time Tb illustrated in FIG. 3, i.e., at a timing at which a lesion candidate region L1 has appeared within the observation image G1 and has been detected by the lesion candidate detection unit 34b. FIG. 6 is a diagram illustrating an example of a display image displayed on the display apparatus through the processing performed in the endoscope image processing apparatus according to the embodiment.

The appearance time calculation unit 38 starts processing for calculating an appearance time period TS based on the observation images G1 sequentially outputted from the video processor 31, the lesion candidate information IL1 outputted from the lesion candidate detection unit 34b, and a determination result outputted from the continued detection determination unit 35 at the timing of the time Tb.

A specific example of processing relating to calculation of an appearance time period TS performed in each of the units in the appearance time calculation unit 38 will be described below.

The region-of-interest reverse tracking unit 38a acquires, based on observation images G1 sequentially outputted from the video processor 31, respective optical flows of the observation images G1 for each frame, and sequentially stores the observation images G1 and the optical flows of the observation images G1 in the memory. The region-of-interest reverse tracking unit 38a acquires, based on an observation image G1N in a frame FN corresponding to a current frame (latest frame) and an observation image G1M in a frame FM preceding the frame FN by one frame, an optical flow of the observation image G1N. The region-of-interest reverse tracking unit 38a reversely tracks, based on the optical flow of the observation image G1N acquired as described above, an optical flow of the observation image G1M stored in the memory, and the lesion candidate information IL1 outputted from the lesion candidate detection unit 34b, a position of a lesion candidate region L1 included in an observation image G1L in a frame FL preceding the frame FM by one frame. The region-of-interest reverse tracking unit 38a consecutively performs the above-described reverse tracking for each frame, to specify a frame immediately before the lesion candidate region L1 is no longer included within the observation image G1 as a frame FA as a frame in which the lesion candidate region L1 has first appeared within the observation image G1.

The region-of-interest reverse tracking unit 38a calculates, based on a number of frames from the frame FA to the frame FN and a frame rate (frames per second) of the observation image G1 outputted from the video processor 31, an image input time period TP as a time period from input of an observation image G1A in the frame FA to the endoscope image processing apparatus 32 until input of the observation image G1N in the frame FN to the endoscope image processing apparatus 32.

That is, the region-of-interest reverse tracking unit 38a consecutively reversely tracks a position of the lesion candidate region L1 for each frame using the observation image G1N in the frame FN as a starting point to specify the observation image G1A in the frame FA while calculating the image input time period TP based on the number of frames from the frame FA to the frame FN.

Note that the region-of-interest reverse tracking unit 38a may not only acquire a vector field constituted by motion vectors of all pixels included in the observation image G1 as an optical flow of the observation image G1 but also acquire a local vector field constituted by a motion vector group of each of pixels included in the lesion candidate region L1 as an optical flow of the observation image G1.

The region-of-interest reverse tracking unit 38a may not only consecutively reversely track the position of the lesion candidate region L1 for each frame but also reversely track the position of the lesion candidate region L1 while skipping the observation image G1 having strong blurring or halation by one or more frames, for example, when the region-of-interest reverse tracking unit 38a specifies the observation image G1A in the frame FA.

The region-of-interest speed estimation unit 38b acquires the optical flow of the observation image G1N based on the observation image G1N and the observation image G1M. The region-of-interest speed estimation unit 38b specifies the motion vector group of each of the pixels included in the lesion candidate region L1 from among motion vectors included in the optical flow of the observation image G1N acquired as described above based on the lesion candidate information IL1 outputted from the lesion candidate detection unit 34b while calculating an estimated movement speed VQ of the lesion candidate region L1 included in the observation image G1N based on the specified motion vector group.

Note that the region-of-interest speed estimation unit 38b may not only perform the above-described processing but also calculate a movement speed of an entire image area (including the lesion candidate region L1 and a background region) based on motion vectors of all pixels included in the optical flow of the observation image G1N while acquiring the calculated movement speed of the entire image area as an estimated movement speed VQ, for example.

The estimated detection time setting unit 38c performs processing for acquiring, based on the observation image G1N and the lesion candidate information IL1 outputted from the lesion candidate detection unit 34b, one or more parameters each representing an image pickup state of the lesion candidate region L1 included in the observation image G1N. The estimated detection time setting unit 38c performs predetermined calculation using the parameters acquired through the above-described processing, to calculate an evaluation value E1 as a value corresponding to a degree of detection difficulty of the lesion candidate region L1.

More specifically, the estimated detection time setting unit 38c performs processing for acquiring, based on the observation image G1N and the lesion candidate information IL1 outputted from the lesion candidate detection unit 34b, at least one of parameters such as a position of the lesion candidate region L1 specified by the lesion candidate information IL1, a size of the lesion candidate region L1 specified by the lesion candidate information IL, a height of a contrast in the observation image G1N, and a strength of a blurring in the observation image G1N, for example, while performing predetermined calculation using the acquired parameter to calculate the evaluation value E1.

The evaluation value E1 is calculated as a relatively large value when the position of the lesion candidate region L1 is close to an edge of the observation image G1N, when the size of the lesion candidate region L1 is small, when the contrast in the observation image G1N is low, and when the blurring in the observation image G1N is strong, for example. The evaluation value E1 is calculated as a relatively small value when the position of the lesion candidate region L1 is close to a center of the observation image G1N, when the size of the lesion candidate region L1 is large, when the contrast in the observation image G1N is high, and when the blurring in the observation image G1N is weak, for example. That is, the evaluation value E1 is calculated as a value which varies depending on whether the degree of detection difficulty of the lesion candidate region L1 is high or low.

The estimated detection time setting unit 38c refers to table data TDA representing a correspondence relationship between the evaluation value E1 calculated by the above-described predetermined calculation and an average detection time period AT previously set as an average time period required to detect the lesion candidate region L1 where the region-of-interest detection unit 34 has appeared within the observation image G1, to specify an evaluation value equal to or closest to the evaluation value E1. The estimated detection time setting unit 38c sets the average detection time period AT corresponding to the evaluation value E1 specified as described above as an estimated detection time period TM as a time period estimated to be required to detect the lesion candidate region L1 in the lesion candidate detection unit 34b.

Figure 7:
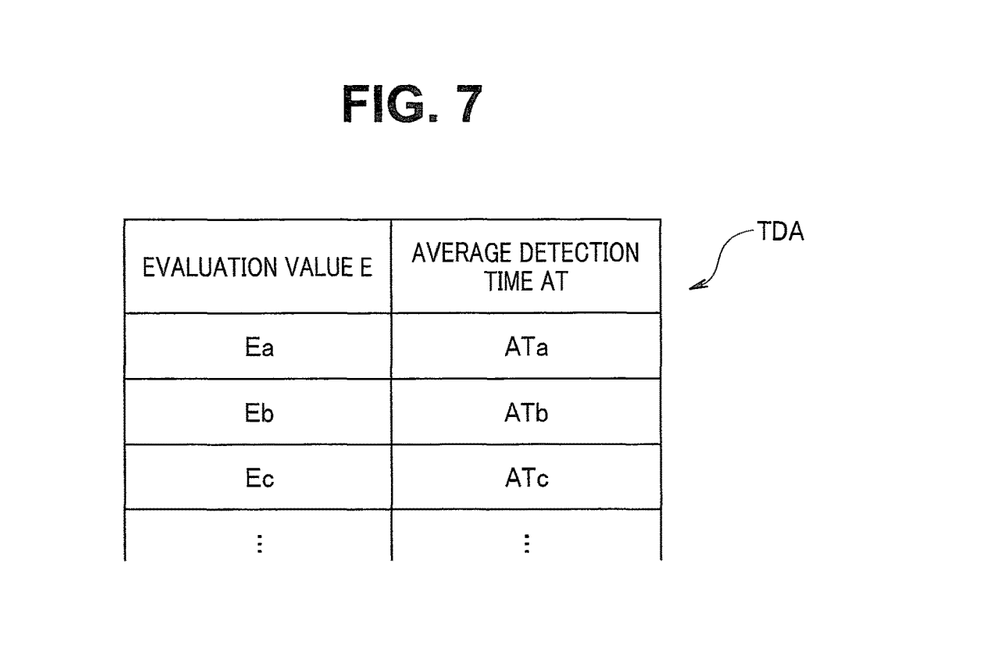
FIG. 7 is a diagram illustrating an example of table data used in the processing performed in the endoscope image processing apparatus according to the embodiment.

Note that the table data TDA is configured as data capable of specifying a correspondence relationship between a plurality of evaluation values Ea, Eb, Ec, . . . and a plurality of average detection time periods ATa, ATb, ATc, . . . , as illustrated in FIG. 7, for example. Therefore, if Eb included in the table data TDA is specified as one equal to or closest to the evaluation value E1, for example, ATb included in the table data TDA is set as an estimated detection time period TM. FIG. 7 is a diagram illustrating an example of table data used in the processing performed in the endoscope image processing apparatus according to the embodiment.

That is, according to the above-described processing, the estimated detection time setting unit 38c sets the estimated detection time period TM based on the one or more parameters each representing the image pickup state of the lesion candidate region L1 included in the observation image G1N.

Note that the estimated detection time setting unit 38c in the present embodiment may calculate the evaluation value E1 and set the estimated detection time period TM using a magnitude of the estimated movement speed VQ of the lesion candidate region L1 in addition to the one or more parameters each representing the image pickup state of the lesion candidate region L1 included in the observation image G1N when a weight coefficient WQ, described below, is a value other than zero, for example. In such a case, the evaluation value E1 can increase as the estimated movement speed VQ increases, and can decrease as the estimated movement speed VQ decreases, for example.

The appearance time measurement unit 38d calculates a shortest distance RN between the edge of the observation image G1N and a position of a center of gravity of the lesion candidate region L1 obtained based on the lesion candidate information IL while calculating an estimated movement time period TQ as a time period estimated to be required until the lesion candidate region L1 moves to a current position after entering the observation image G1 based on the calculated shortest distance RN and the estimated movement speed VQ calculated by the region-of-interest speed estimation unit 38b. More specifically, the appearance time measurement unit 38d divides the shortest distance RN by |VQ| as the magnitude of the estimated movement speed VQ (=RN/|VQ|), to calculate the estimated movement time period TQ.

The appearance time measurement unit 38d calculates, based on the estimated detection time period TM set by the estimated detection time setting unit 38c and the continued detection time period TK measured using the timing of the time Tb illustrated in FIG. 3 as a starting point, an estimated elapsed time period TR as a time period obtained by estimating an elapsed time period from appearance of the lesion candidate region L1 within the observation image G1 depending on a situation where the lesion candidate detection unit 34b detects the lesion candidate region L1. More specifically, the appearance time measurement unit 38d adds the estimated detection time period TM and the continued detection time period TK (=TM+TK), to calculate the estimated elapsed time period TR.

The appearance time measurement unit 38d applies the image input time period TP, the estimated movement time period TQ, and the estimated elapsed time period TR to a numerical equation (1), described below, to calculate an appearance time period TS.

$$TS = \frac{TP \times WP + TQ \times WQ + TR \times WR}{WP + WQ + WR} \quad (1)$$

Note that WP, WQ, and WR in the above-described numerical equation (1) respectively represent weight coefficients set as values belonging to a predetermined range of 0 or more and 1 or less, for example. WP, WQ, and WR in the above-described numerical equation (1) are respectively calculated as likelihoods as values representing probabilities of the image input time period TP, the estimated movement time period TQ, and the estimated elapsed time period TR, for example.

According to processing using the above-described numerical equation (1), if WP=WQ=WR=1 is set, for example, an average value of the image input time period TP, the estimated movement time period TQ, and the estimated elapsed time period TR is calculated as the appearance time period TS. According to the processing using the above-described numerical equation (1), if WQ=WR=0 is set, for example, a value obtained by multiplying the image input time period TP by the weight coefficient WP (=TP×WP) is calculated as the appearance time period TS. According to the processing using the above-described numerical equation (1), if WP=WR=0 is set, for example, a value obtained by multiplying the estimated movement time period TQ by the weight coefficient WQ (=TQ×WQ) is calculated as the appearance time period TS. According to the processing using the above-described numerical equation (1), if WP=WQ=0 is set, for example, a value obtained by multiplying the estimated elapsed time period TR by the weight coefficient WR (=TR×WR) is calculated as the appearance time period TS. According to the processing using the above-described numerical equation (1), any one of the weight coefficients WP, WQ, and WR may be set to zero to calculate the appearance time period TS.

That is, according to the processing as described above, the appearance time measurement unit 38d calculates the appearance time period TS based on at least one of the image input time period TP, the estimated movement time period TQ, and the estimated elapsed time period TR.

The appearance time calculation unit 38 repeatedly performs the processing as illustrated above until immediately before a timing of the time Td illustrated in FIG. 3, i.e., a timing at which the lesion candidate region L1 disappears from within the observation image G1, to calculate the appearance time period TS in real time while outputting the calculated appearance time period TS to the display control unit 36.

Figure 8:
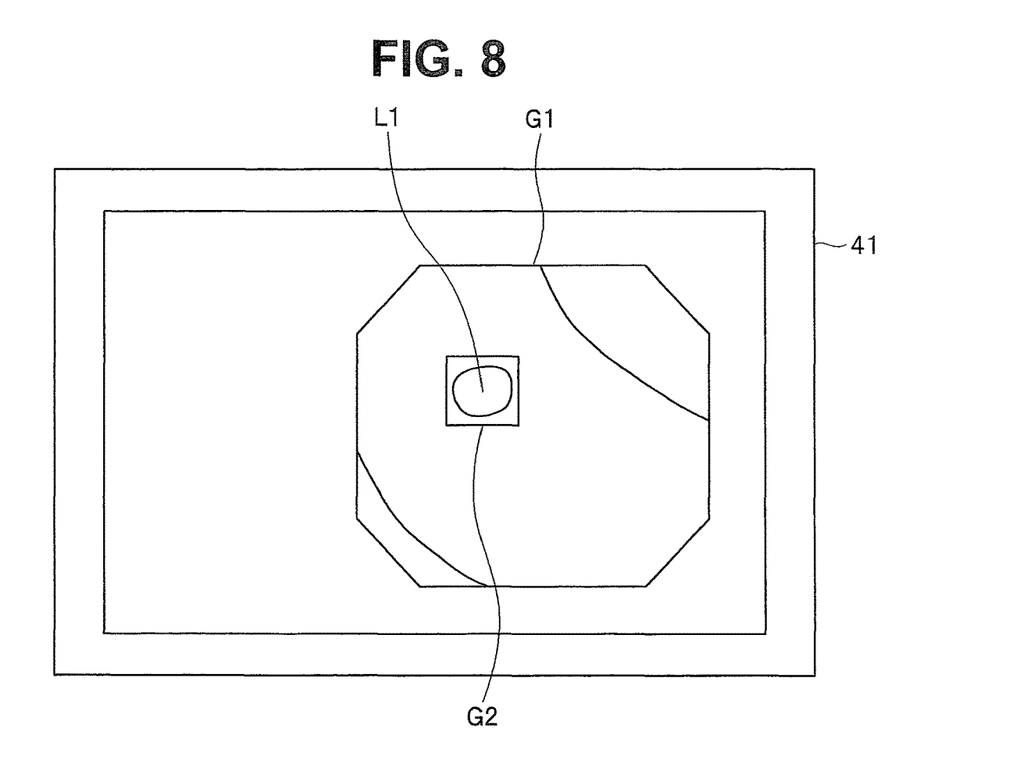
FIG. 8 is a diagram illustrating an example of a display image displayed on the display apparatus through the processing performed in the endoscope image processing apparatus according to the embodiment.
Figure 9:
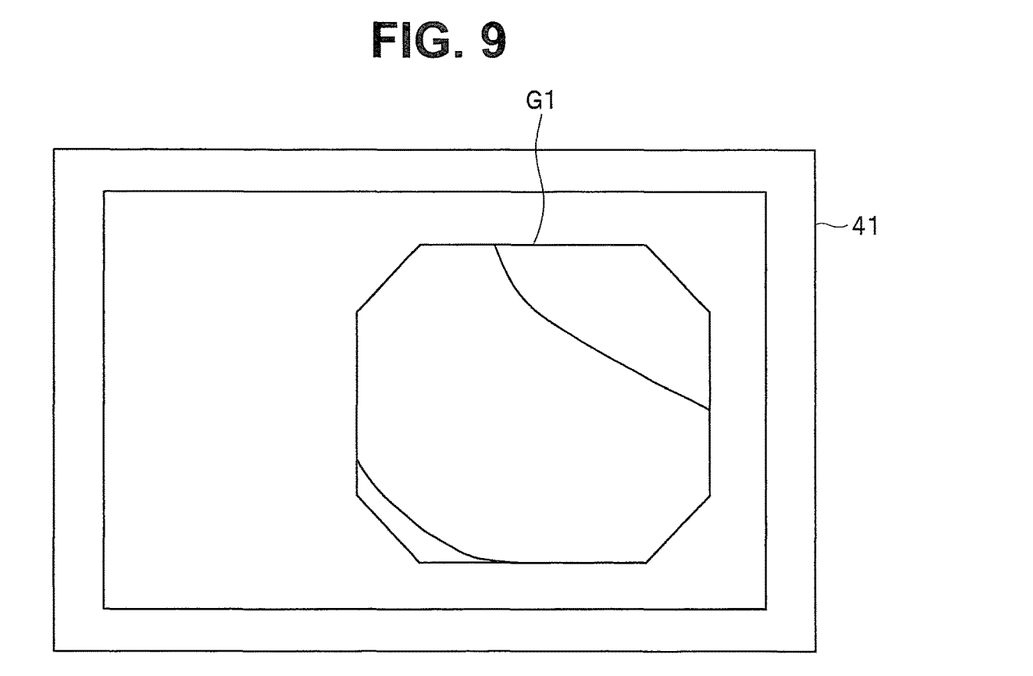
FIG. 9 is a diagram illustrating an example of a display image displayed on the display apparatus through the processing performed in the endoscope image processing apparatus according to the embodiment.

The emphasis processing unit 36a in the display control unit 36 starts emphasis processing for adding a marker image G2 for emphasizing the position of the lesion candidate region L1 to the observation image G1 at a timing of the time Tc illustrated in FIG. 3, i.e., a timing at which the appearance time period TS calculated by the appearance time measurement unit 38d has reached a predetermined time period TH. The emphasis processing unit 36a in the display control unit 36 stops the above-described emphasis processing at the timing of the time Td illustrated in FIG. 3. According to such an operation of the display control unit 36, an observation image G1 including the marker image G2, as illustrated in FIG. 8, for example, is displayed on the screen of the display apparatus 41 at the timing of the time Tc. According to the above-described operation of the display control unit 36, an observation image G1 as illustrated in FIG. 9, for example, is displayed on the screen of the display apparatus 41 at the timing of the time Td. FIGS. 8 and 9 are diagrams each illustrating an example of a display image displayed on the display apparatus through the processing performed in the endoscope image processing apparatus according to the embodiment.

In a time period from the time Ta to immediately before the time Tb, there can occur a situation where at least a part of the lesion candidate region L1 has appeared within the observation image G1 while the detection of the lesion candidate region L1 by the region-of-interest detection unit 34 (the lesion candidate detection unit 34b) has not been completed. Therefore, if measurement of the predetermined time period TH has been started using the timing of the time Tc corresponding to a timing at which the detection of the lesion candidate region L1 by the region-of-interest detection unit 34 has been completed as a starting point, for example, it is considered that a timing at which the emphasis processing for emphasizing the position of the lesion candidate region L1 is started is delayed by a time period required to detect the lesion candidate region L1. Therefore, if the measurement of the predetermined time period TH has been started using the timing of the time Tc illustrated in FIG. 3 as a starting point, it is considered that as a frequency of occurrence of the lesion candidate region L1, which disappears from within the observation image G1 while not being subjected to the emphasis processing by the emphasis processing unit 36a despite appearing within the observation image G1, increases, a lesion portion is easily overlooked by operator's visual observation.

On the other hand, according to the respective operations of the display control unit 36 and the appearance time calculation unit 38, as described above, the appearance time period TS as the elapsed time period from appearance of the lesion candidate region L1 within the observation image G1 is calculated while the emphasis processing by the emphasis processing unit 36a is started at the timing at which the appearance time period TS has reached the predetermined time period TH. Accordingly, the lesion portion can be prevented from being overlooked by operator's visual observation as much as possible. That is, according to the present embodiment, the region of interest can be presented to an operator without preventing an attention to the observation image G1 from decreasing and preventing an ability to find a lesion portion from being improved.

The image processing apparatus and the like according to the present embodiment may include a processor and a storage (e.g., a memory). The functions of individual units in the processor may be implemented by respective pieces of hardware or may be implemented by an integrated piece of hardware, for example. The processor may include hardware, and the hardware may include at least one of a circuit for processing digital signals and a circuit for processing analog signals, for example. The processor may include one or a plurality of circuit devices (e.g., an IC) or one or a plurality of circuit elements (e.g., a resistor, a capacitor) on a circuit board, for example. The processor may be a CPU (Central Processing Unit), for example, but this should not be construed in a limiting sense, and various types of processors including a GPU (Graphics Processing Unit) and a DSP (Digital Signal Processor) may be used. The processor may be a hardware circuit with an ASIC (Application Specific Integrated Circuit) or an FPGA (Field-Programmable Gate Array). The processor may include an amplification circuit, a filter circuit, or the like for processing analog signals. The memory may be a semiconductor memory such as an SRAM and a DRAM; a register; a magnetic storage device such as a hard disk device; and an optical storage device such as an optical disk device. The memory stores computer-readable instructions, for example. When the instructions are executed by the processor, the functions of each unit of the image processing device and the like are implemented. The instructions may be a set of instructions constituting a program or an instruction for causing an operation on the hardware circuit of the processor.

The units in the image processing apparatus and the like and the display apparatus according to the present embodiment may be connected with each other via any types of digital data communication such as a communication network or via communication media. The communication network may include a LAN (Local Area Network), a WAN (Wide Area Network), and computers and networks which form the internet, for example.

What is claimed is:

1. An endoscope image processing apparatus comprising:
a region-of-interest detection apparatus configured to sequentially receive observation images obtained by performing image pickup of an object and to perform processing for detecting a region of interest for each of the observation images; and
a processor, the processor being configured to:
calculate an appearance time period as an elapsed time period from a first timing at which at least a part of the region of interest appears within the observation image, the first timing differing from a second timing at which the region-of-interest detection apparatus detects the region of interest, and
start emphasis processing for emphasizing a position of the region of interest existing within the observation image at a timing at which the appearance time period reaches a predetermined time period,
wherein the processor calculates the appearance time period based on a first time period as a time period from a time when the observation image in a first frame as a frame where one region of interest detected by the region-of-interest detection apparatus first appears is inputted to the region-of-interest detection apparatus until the observation image in a second frame as a current frame is inputted to the region-of-interest detection apparatus, and
wherein the processor reversely tracks a position of the one region of interest using the observation image in the second frame as a starting point to specify the observation image in the first frame, and calculates the first time period based on a number of frames from the first frame to the second frame.

2. An endoscope image processing apparatus comprising:
a region-of-interest detection apparatus configured to sequentially receive observation images obtained by performing image pickup of an object and to perform processing for detecting a region of interest for each of the observation images; and
a processor, the processor being configured to:
calculate an appearance time period as an elapsed time period from a first timing at which at least a part of the region of interest appears within the observation image, the first timing differing from a second timing at which the region-of-interest detection apparatus detects the region of interest, and
start emphasis processing for emphasizing a position of the region of interest existing within the observation image at a timing at which the appearance time period reaches a predetermined time period,
wherein the processor calculates the appearance time period based on a second time period as a time period estimated to be required until one region of interest detected by the region-of-interest detection apparatus moves to a current position after entering the observation image, and
wherein the processor calculates the second time period based on an estimated movement speed of the one region of interest included in the observation image in a current frame.

3. An endoscope image processing apparatus comprising:
a region-of-interest detection apparatus configured to sequentially receive observation images obtained by performing image pickup of an object and to perform processing for detecting a region of interest for each of the observation images; and
a processor, the processor being configured to:
calculate an appearance time period as an elapsed time period from a first timing at which at least a part of the region of interest appears within the observation image, the first timing differing from a second timing at which the region-of-interest detection apparatus detects the region of interest, and
start emphasis processing for emphasizing a position of the region of interest existing within the observation image at a timing at which the appearance time period reaches a predetermined time period,
wherein the processor is configured to calculate the appearance time period based on a third time period as a time period obtained by estimating the elapsed time period depending on a situation where the region-of-interest detection apparatus detects one region of interest, and
wherein the processor calculates the third time period based on an estimated detection time period as a time period estimated to be required to detect the one region of interest in the region-of-interest detection apparatus and a continued detection time period as an elapsed time period from a time when the region-of-interest detection apparatus starts to detect the one region of interest.

4. The endoscope image processing apparatus according to claim 3, wherein the processor sets the estimated detection time period based on one or more parameters each representing an image pickup state of the one region of interest included in the observation image in a current frame.

* * * * *